US009897624B2

(12) United States Patent
Tamezane et al.

(10) Patent No.: US 9,897,624 B2
(45) Date of Patent: Feb. 20, 2018

(54) AUTOMATIC ANALYZER (71) Applicant: HITACHI HIGH-TECHNOLOGIES CORPORATION, Tokyo (JP)

(72) Inventors: Hideto Tamezane, Tokyo (JP); Isao Yamazaki, Tokyo (JP); Masaharu Nishida, Tokyo (JP); Kumiko Kamihara, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 159 days.

(21) Appl. No.: 14/410,113

(22) PCT Filed: Jun. 20, 2013

(86) PCT No.: PCT/JP2013/066987
§ 371 (c)(1),
(2) Date: Dec. 22, 2014

(87) PCT Pub. No.: WO2014/013836
PCT Pub. Date: Jan. 23, 2014

(65) Prior Publication Data
US 2015/0323557 A1 Nov. 12, 2015

(30) Foreign Application Priority Data
Jul. 20, 2012 (JP) ................. 2012-162026

(51) Int. Cl.
G01N 35/10 (2006.01)
G01N 35/00 (2006.01)
(52) U.S. Cl.
CPC ... *G01N 35/1016* (2013.01); *G01N 35/00584* (2013.01); *G01N 35/00663* (2013.01);
(Continued)
(58) Field of Classification Search
None
See application file for complete search history.

(56) References Cited

U.S. PATENT DOCUMENTS

2004/0034479 A1* 2/2004 Shimase ............ G01N 35/1016
702/19
2009/0000401 A1* 1/2009 Oonuma ............ G01N 35/1011
73/864.11
(Continued)

FOREIGN PATENT DOCUMENTS

EP 2 026 076 A1 2/2009
EP 2 037 283 A1 3/2009
(Continued)

OTHER PUBLICATIONS

Extended European Search Report received in corresponding European Application No. 13819196.0 dated Feb. 22, 2016.
International Preliminary Report on Patentability received in International Application No. PCT/JP2013/066987 dated Jan. 29, 2015.

*Primary Examiner* — Jill A Warden
*Assistant Examiner* — Benjamin R Whatley
(74) *Attorney, Agent, or Firm* — Mattingly & Malur, PC (57) ABSTRACT An automatic analyzer that accurately detects dispensation abnormality in dispensation conditions with small suction quantities has a statistical distance calculation unit that calculates characteristic variables regarding a sucking operation in the first dispensation and calculates a statistical distance D from reference data to the characteristic variables extracted from a memory. A comparison unit compares the statistical distance D with a preset threshold value stored in memory and if the statistical distance D is less than the preset threshold value, the first discharging operation is performed. A controller judges whether a single-handed judgment based on a dispensation quantity condition of the second or subsequent dispensation is possible or not. If the single-handed judgment is impossible, reference data is selected based on a judgment quantity regarding the first dispensation. Whether the sucking operation in the second or (Continued)

subsequent dispensation is normal or abnormal is judged based on the selected reference data.

5 Claims, 9 Drawing Sheets

(52) U.S. Cl.
CPC ..... *G01N 35/1002* (2013.01); *G01N 35/1009* (2013.01); *G01N 2035/00673* (2013.01); *G01N 2035/1018* (2013.01); *G01N 2035/1025* (2013.01)

(56) References Cited

U.S. PATENT DOCUMENTS

| | | | | |
|---|---|---|---|---|
| 2009/0070049 | A1* | 3/2009 | Ziegler | G01N 35/1016 |
| | | | | 702/50 |
| 2011/0236990 | A1* | 9/2011 | Mizutani | G01N 35/00603 |
| | | | | 436/180 |

FOREIGN PATENT DOCUMENTS

| | | |
|---|---|---|
| JP | 2004-125780 A | 4/2004 |
| JP | 2004-177308 A | 6/2004 |
| JP | 2004-271266 A | 9/2004 |
| JP | 2008-224691 A | 9/2008 |

\* cited by examiner

P0 ··· PRESSURE SENSOR OUTPUT JUST BEFORE START OF SUCTION AFTER LIQUID LEVEL DETECTION

P1 ··· PRESSURE SENSOR OUTPUT JUST BEFORE END OF SUCTION

FIG. 7

| DIFFERENTIAL PRESSURE | REFERENCE DATA | CONSIDERED VISCOSITY (mPa·s) |
|---|---|---|
| $Pa \leq X < Pb$ | I | 0.9-1.6 |
| $Pb \leq X < Pc$ | II | 1.6-2.3 |
| $Pc \leq X < Pd$ | III | 2.3-3.0 |

REFERENCE DATA III IS SELECTED WHEN CALCULATED DIFFERENTIAL PRESSURE $\Delta P$ IS WITHIN RANGE $Pc \leq X < Pd$

FIG. 8

| CHARACTERISTIC VARIABLE No. / EVENT No. | 1 | 2 | ... | k-1 | k |
|---|---|---|---|---|---|
| 1 | $x_{11}$ | $x_{12}$ | ... | $x_{1k-1}$ | $x_{1k}$ |
| 2 | $x_{21}$ | $x_{22}$ | ... | $x_{2k-1}$ | $x_{2k}$ |
| ⋮ | ... | ... | ... | ... | ... |
| n-1 | $x_{n-11}$ | $x_{n-12}$ | ... | $x_{n-1k-1}$ | $x_{n-1k}$ |
| n | $x_{n1}$ | $x_{n2}$ | ... | $x_{nk-1}$ | $x_{nk}$ |

|  | FIRST | SECOND | THIRD | FOURTH |
|---|---|---|---|---|
| DISPENSATION QUANTITY | 2.0ul | 1.2ul | 8.0ul | 3.5ul |
| DUMMY QUANTITY | 10.0ul | — | — | — |
| DISCHARGE QUANTITY | 2.0ul | 1.2ul | 8.0ul | 3.5ul |
| SINGLE-HANDED JUDGMENT | ◯ |  | ◯ |  |
| JUDGMENT BY USING INFORMATION ON FIRST DISPENSATION | — | ◯ |  | ◯ |

FIG. 11

(a) NOT INCORPORATING INFORMATION ON FIRST DISPENSATION (b) INCORPORATING INFORMATION ON FIRST DISPENSATION

| CHARACTERISTIC VARIABLE No.<br>EVENT No. | FIRST SUCTION | | | | | | n-TH DISPENSATION (n≥2) OF JUDGMENT OBJECT | | | |
|---|---|---|---|---|---|---|---|---|---|---|
| | 1 | 2 | 3 | 4 | ... | ... | k-3 | k-2 | k-1 | k |
| 1 | $x_{11}$ | $x_{12}$ | $x_{13}$ | $x_{14}$ | ... | ... | $x_{1k-3}$ | $x_{1k-2}$ | $x_{1k-1}$ | $x_{1k}$ |
| 2 | $x_{21}$ | $x_{22}$ | $x_{23}$ | $x_{24}$ | ... | ... | $x_{2k-3}$ | $x_{2k-2}$ | $x_{2k-1}$ | $x_{2k}$ |
| ⋮ | ... | ... | ... | ... | ... | ... | ... | ... | ... | ... |
| n-1 | $x_{n-11}$ | $x_{n-12}$ | $x_{n-13}$ | $x_{n-14}$ | ... | ... | $x_{n-1k-3}$ | $x_{n-1k-2}$ | $x_{n-1k-1}$ | $x_{n-1k}$ |
| n | $x_{n1}$ | $x_{n2}$ | $x_{n3}$ | $x_{n4}$ | ... | ... | $x_{nk-3}$ | $x_{nk-2}$ | $x_{nk-1}$ | $x_{nk}$ |

AUTOMATIC ANALYZER

TECHNICAL FIELD

The present invention relates to an automatic analyzer comprising a sample dispensation device.

BACKGROUND ART

In an automatic analyzer such as a biochemical automatic analyzer, for the component analysis of a biological sample (blood serum, urine, etc.), the sample and a reagent are brought into reaction and changes in the color tone and the turbidity caused by the reaction are optically measured by a photometric measurement unit such as a spectrophotometer.

For the reaction of the sample and the reagent, dispensation of the sample and the reagent from vessels storing them to a reaction vessel has to be carried out. Therefore, such an automatic analyzer is equipped with a dispensation device capable of automatically performing the suction of a sample/reagent from a vessel storing the sample/reagent and the discharging of the sample/reagent into a reaction vessel.

In a sample dispensation device for dispensing a sample from a sample vessel to a reaction vessel, dispensation abnormality can occur due to various factors. The sample dispensation device has a probe for sucking in and discharging the sample. The clogging of the probe caused by suction of solid foreign objects (e.g., fibrin) is a frequent cause of the dispensation abnormality. The clogging of the probe makes it impossible to accurately dispense the prescribed amount of sample to the reaction vessel and acquire reliable analysis result.

Further, when an air bubble or a liquid membrane exists on the liquid surface of the sample, the air bubble or the liquid membrane can be detected as the liquid surface. This disables the suction of the necessary amount of sample and causes the dispensation abnormality.

In order to avoid the dispensation abnormality caused by the existence of an air bubble or a liquid membrane, it is possible to increase the immersion depth of the probe in the sample. However, increasing the probe's immersion depth in the sample can lead to an increase in the contamination and an adverse effect on the analysis result.

Therefore, the operation of the probe is generally controlled by the following method in order to reduce the probe's immersion depth in the liquid as much as possible: First, the surface of the liquid in the vessel is detected. The downward movement of the probe is stopped at a position where the tip end of the probe is situated slightly below the liquid surface. Thereafter, a prescribed amount of liquid is sucked into the probe.

As a method for detecting the liquid surface of the sample, the capacitance change method (detecting a change in capacitance when the probe makes contact with the liquid surface) is the most commonly used. However, if the aforementioned air bubble or liquid membrane exists on the liquid surface when such a liquid level sensor is used, the liquid level sensor can erroneously detect the air bubble or the liquid membrane as the liquid surface and cause the dispensation abnormality.

Many technologies have been proposed as means for judging the occurrence of the above-described dispensation abnormality, in which a pressure sensor is arranged in a dispensation channel including the sample probe and the dispensation abnormality (e.g., the clogging of the sample probe) is detected based on pressure fluctuation.

In a technology disclosed in Patent Literature 1, data generated from time-series data of the pressure when the suction was performed normally is used as reference data. Meanwhile, time-series data of the output value of the pressure sensor at the time of the suction is used as comparative data. Abnormality in the suction is detected based on the Mahalanobis distance calculated from the reference data and the comparative data.

According to the technology described in the Patent Document 1, the reference data is prepared corresponding to each dispensation condition including the dispensation quantity, and thus the abnormality can be detected accurately even in different dispensation conditions. Further, since the abnormality detection is carried out by calculating the Mahalanobis distance based on the time-series data of the pressure across the entire period from the start of the suction to a time after the end of the suction, not only an abnormality caused by a particular factor but also abnormalities caused by a variety of factors can be detected.

PRIOR ART DOCUMENT

Patent Document

Patent Document 1: JP-2008-224691-A

SUMMARY OF THE INVENTION

Problem to be Solved by the Invention

However, the method described in the Patent Document 1 involves a problem in that there are cases where the detection of the dispensation abnormality is difficult in dispensation conditions with small suction quantities. For example, suction of a minute foreign object or an air bubble into the probe corresponds to such cases. The pressure fluctuation in such cases generally tends to be relatively closer to the pressure fluctuation in the case of normal dispensation, compared to cases where the probe has been totally clogged up or has sucked in a highly viscous sample.

Specifically, in dispensation conditions with small suction quantities, the time of the sucking/discharging operation is short and the pressure information that can be acquired from the sucking/discharging operation is necessitated to be limited. Since it is required to detect a slight change from a limited amount of information, the detection of the dispensation abnormality is difficult in such conditions.

It is therefore the object of the present invention to implement an automatic analyzer capable of performing highly reliable analysis by accurately detecting the dispensation abnormality in dispensation conditions with small suction quantities. Especially in the second and subsequent dispensations of the same sample, the suction quantity decreases due to the unnecessity of suction of a dummy quantity and that can make the accurate detection of the dispensation abnormality difficult.

Means for Solving the Problem

To achieve the above object, the present invention is configured as described below.

A typical configuration of the present invention is as follows:

(1) An automatic analyzer comprising: a sample probe which sucks in a sample stored in a sample vessel and discharges the sample into a reaction vessel; a reagent probe which sucks in a reagent stored in a reagent vessel and discharges the reagent into the reaction vessel; an analysis unit which analyzes the sample in the reaction vessel; a pressure sensor which detects the pressure in the sample probe; a signal processing unit which is configured to acquire suction pressure data of the sample sucked in from the sample vessel and discharged into the reaction vessel by the sample probe in the first dispensation from the pressure sensor, select a piece of normality/abnormality judgment reference data from multiple pieces of normality/abnormality judgment reference data based on the suction pressure data in cases where the same sample is sucked in from the sample vessel and discharged into the reaction vessel by the sample probe in the n-th dispensation (n: natural number greater than 1), calculate characteristic variables of the suction pressure data of the same sample detected by the pressure sensor in the n-th dispensation by the sample probe, and judge whether there was an abnormality in the suction of the sample by the sample probe or not by comparing the calculated characteristic variables with the normality/abnormality judgment reference data; and a controller which controls the operation of the sample probe, the reagent probe, the analysis unit and the signal processing unit.

Another typical configuration of the present invention is as follows:

(2) An automatic analyzer comprising: a sample probe which sucks in a sample stored in a sample vessel and discharges the sample into a reaction vessel; a reagent probe which sucks in a reagent stored in a reagent vessel and discharges the reagent into the reaction vessel; an analysis unit which analyzes the sample in the reaction vessel; a pressure sensor which detects the pressure in the sample probe; a signal processing unit which is configured to calculate characteristic variables of suction pressure data detected by the pressure sensor in the suction from the sample vessel and the discharge into the reaction vessel in the first dispensation by the sample probe, calculate the characteristic variables of the suction pressure data detected by the pressure sensor in the n-th dispensation (n: natural number, 2≤n) and calculates judgment object data regarding the n-th dispensation as a combination of the characteristic variables regarding the first dispensation and the characteristic variables regarding the n-th dispensation in cases where the same sample is sucked in from the sample vessel and discharged into the reaction vessel by the sample probe in the n-th dispensation (n: natural number greater than 1), and judge whether there was an abnormality in the suction of the sample by the sample probe or not by comparing the judgment object data with reference data as a combination of normality/abnormality judgment reference data corresponding to the sample suction quantity in the first dispensation and normality/abnormality judgment reference data corresponding to the sample suction quantity in the n-th dispensation; and a controller which controls the operation of the sample probe, the reagent probe, the analysis unit and the signal processing unit.

Still another typical configuration of the present invention is as follows:

(3) An automatic analyzer comprising: a sample probe which sucks in a sample stored in a sample vessel and discharges the sample into a reaction vessel; a reagent probe which sucks in a reagent stored in a reagent vessel and discharges the reagent into the reaction vessel; an analysis unit which analyzes the sample in the reaction vessel; a pressure sensor which detects the pressure in the sample probe; a signal processing unit which is configured to calculate characteristic variables of suction pressure data detected by the pressure sensor in the suction from the sample vessel and the discharge into the reaction vessel in the first dispensation by the sample probe, calculate the characteristic variables of the suction pressure data detected by the pressure sensor in the n-th dispensation (n: natural number, 2≤n) and calculates judgment object data regarding the n-th dispensation as a combination of the characteristic variables regarding the first dispensation and the characteristic variables regarding the n-th dispensation in cases where the same sample is sucked in from the sample vessel and discharged into the reaction vessel by the sample probe in the n-th dispensation (n: natural number greater than 1), and judge whether there was an abnormality in the suction of the sample by the sample probe or not by comparing the judgment object data with reference data as a combination of first normality/abnormality judgment reference data corresponding to the sample suction quantity in the first dispensation and second normality/abnormality judgment reference data selected from multiple pieces of normality/abnormality judgment reference data based on the sample suction quantity in the n-th dispensation and the suction pressure data detected by the pressure sensor; and a controller which controls the operation of the sample probe, the reagent probe, the analysis unit and the signal processing unit.

Effect of the Invention

According to the present invention, an automatic analyzer capable of performing highly reliable analysis by accurately detecting the dispensation abnormality in dispensation conditions with small suction quantities is implemented. Especially, an automatic analyzer capable of performing highly reliable analysis by accurately detecting the abnormality in the second and subsequent dispensations of the same sample is implemented.

MODE FOR CARRYING OUT THE INVENTION

Referring now to the drawings, a description will be given in detail of preferred embodiments of the present invention.

EMBODIMENTS

First Embodiment

Figure 1:
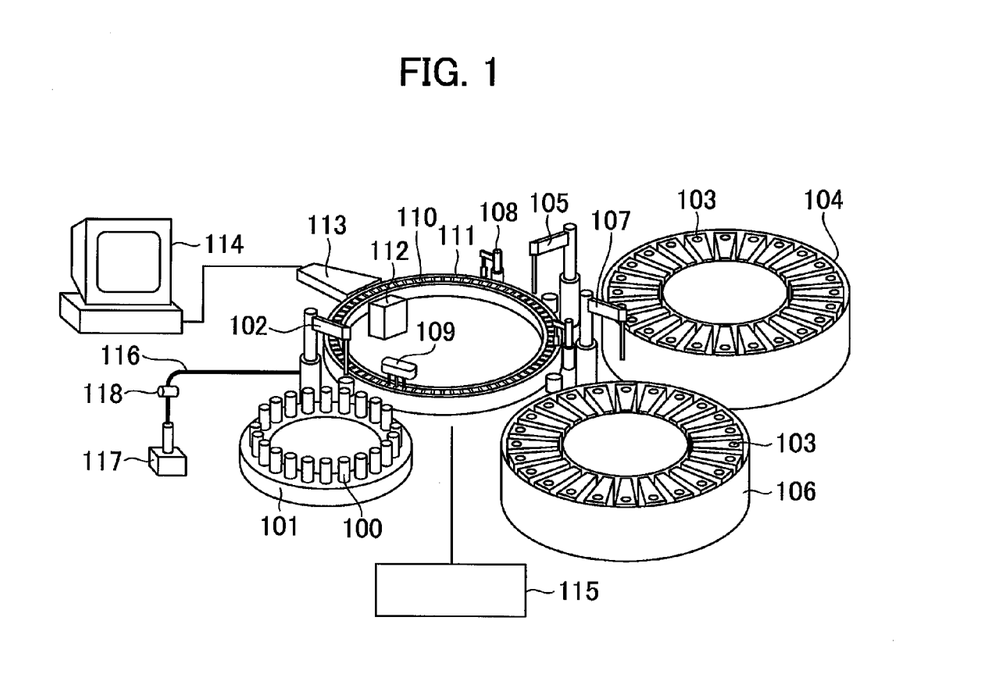
FIG. 1 is a schematic diagram showing the overall configuration of an automatic analyzer to which the present invention is applied.

FIG. 1 is a schematic diagram showing the overall configuration of an automatic analyzer to which the present invention is applied.

Referring to FIG. 1, the automatic analyzer comprises a sample disk 101 on which a plurality of sample vessels 100 storing samples can be mounted, first and second reagent disks 104 and 106 on each of which a plurality of reagent vessels 103 storing reagents can be mounted, and a reaction disk 111 on which a plurality of reaction vessels 110 are arranged along the periphery of the disk.

The automatic analyzer further comprises a sample probe 102 for dispensing a sample sucked in from a sample vessel 100 into a reaction vessel 110, a first reagent probe 105 for dispensing a reagent sucked in from a reagent vessel 103 on the first reagent disk 104 into a reaction vessel 110, and a second reagent probe 107 for dispensing a reagent sucked in from a reagent vessel 103 on the second reagent disk 106 into a reaction vessel 110.

The automatic analyzer further comprises a stirring device 108 for stirring the liquid in each reaction vessel 110, a vessel cleaning mechanism 109 for cleaning the reaction vessels 110, a light source 112 arranged in the vicinity of the inner circumference of the reaction disk 111, a spectroscopic detector 113, a computer 114 connected to the spectroscopic detector 113, and a controller 115 for controlling the operation of the entire automatic analyzer and communicating data with external devices.

The sample probe 102 is connected to a metering pump 117 via a dispensation channel 116. A pressure sensor 118 is arranged in the middle of the dispensation channel 116.

Figure 2:
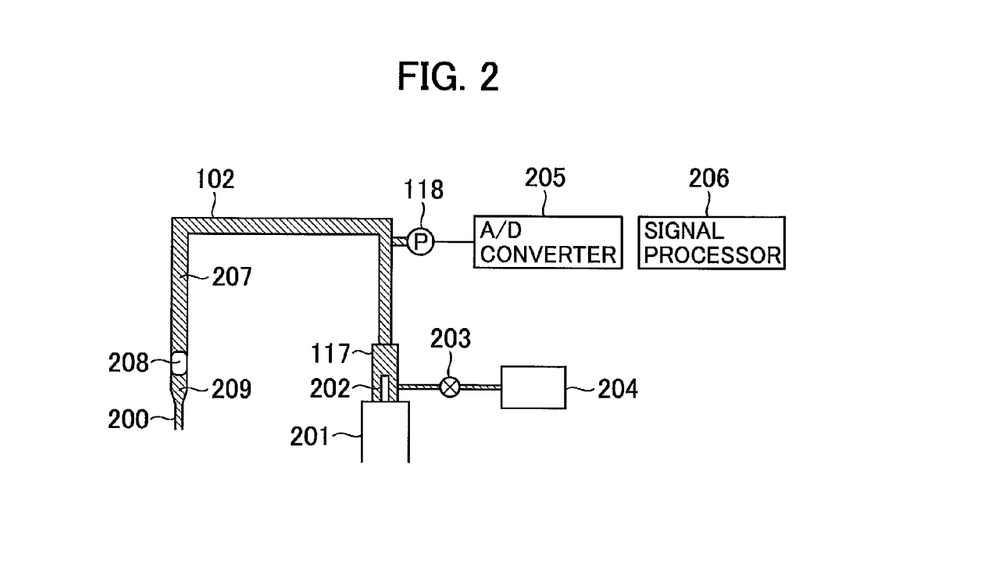
FIG. 2 is an explanatory drawing of a principal part (pressure signal processing unit) in a first embodiment of the present invention.

FIG. 2 is an explanatory drawing of a principal part (pressure signal processing unit in the sample probe 102) in the first embodiment of the present invention.

Referring to FIG. 2, at the tip end of the sample probe 102, a restrictor part 200 is formed to have a smaller cross-sectional area than the other parts. The metering pump 117 is equipped with a plunger 202 which is driven by a drive mechanism 201. The metering pump 117 is connected with a pump 204 via a valve 203.

The pressure sensor 118 is connected to a signal processor (signal processing unit) 206 via an A/D converter 205. The sample probe 102 is filled with a system liquid 207. A sample 209 is sucked into the sample probe 102 via separation air 208. FIG. 2 shows a state in which the sample 209 has been sucked into the sample probe 102.

The sample probe 102 is equipped with a moving mechanism (unshown). The moving mechanism is capable of moving the sample probe 102 to a sample vessel 100 and to a reaction vessel 110 by vertically moving and rotating the sample probe 102.

Next, the operation in the first embodiment of the present invention will be described below.

Referring to FIGS. 1 and 2, a sample vessel 100 is filled with a sample as an inspection object (e.g., blood serum) and is set on the sample disk 101. Information on the types of analysis necessary for each sample is input to the controller 115 from the computer 114. The sample extracted from the sample vessel 100 by the sample probe 102 is dispensed into a reaction vessel 110 on the reaction disk 111 up to a prescribed amount.

Then, a prescribed amount of reagent is dispensed from a reagent vessel 103 on the first reagent disk 104 or the second reagent disk 106 to the reaction vessel 110 by the first reagent probe 105 or the second reagent probe 107. The mixture of the sample and the reagent in the reaction vessel 110 is stirred by the stirring device 108. The amounts of the sample and the reagent to be dispensed to the reaction vessel 110 have been set previously for each type of analysis.

The reaction disk 111 repeats rotating and stopping periodically. Photometric measurement by the spectroscopic detector 113 is performed at the time when the reaction vessel 110 passes in front of the light source 112. The spectroscopic detector 113 repeats the photometric measurement during a 10-minute reaction time. Thereafter, the discharging of the reaction solution from the reaction vessel 110 and the cleaning of the reaction vessel 110 are performed by the vessel cleaning mechanism 109. In the meantime, operations using other samples and reagents are conducted in parallel in other reaction vessels 110. Data obtained by the photometric measurement by the spectroscopic detector 113 are used for calculation by the computer 114. The concentration of each component corresponding to the type of the analysis is calculated and the result of the calculation is displayed on a display unit of the computer 114.

The operation of the sample probe 102 will be explained in detail below.

Before the suction of the sample, the controller 115 opens and closes the valve 203 and thereby fills the channel of the sample probe 102 with the system liquid 207 supplied from the pump 204. Subsequently, with the tip end of the sample probe 102 held in the air, the controller 115 controls the drive mechanism 201 so as to lower the plunger 202 and thereby make the sample probe 102 suck in the separation air 208.

Subsequently, the controller 115 lowers the sample probe 102 into the sample vessel 100. With the tip end of the sample probe 102 immersed in the sample, the plunger 202 is lowered for a prescribed distance, by which the sample is sucked into the sample probe 102. In this case, the liquid 209 that is sucked in is the sample. Pressure fluctuation in the sample probe 102 during the operation from the suction is detected by the pressure sensor 118, converted into a digital signal by the A/D converter 205, and sent to the signal processor 206. Thereafter, the sample probe 102 is moved to a position over a reaction vessel 110 and the sample is discharged from the sample probe 102.

Pressure fluctuation in the sample probe 102 during the operation from the time of discharging the sample is detected again by the pressure sensor 118, converted into a digital signal by the A/D converter 205, and sent to the signal processor 206. Subsequently, the inside and outside of the sample probe 102 are cleaned by opening and closing the valve 203. Thereafter, the sample probe 102 stays on standby for the next analysis.

The signal processor 206 judges the presence/absence of an abnormality in the dispensation based on pressure waveforms of the sample probe 102 at the times of sample suction and sample discharge. When the signal processor 206 judges that there was an abnormality, the analysis is interrupted, an alarm is displayed on the display unit of the computer 114, for example, and a resuming operation is carried out. The resuming operation is selected from several types of operations such as "removing the cause of the abnormality and performing the dispensation again", "moving onto the inspection of another sample", and "stopping the analyzer".

Figure 3:
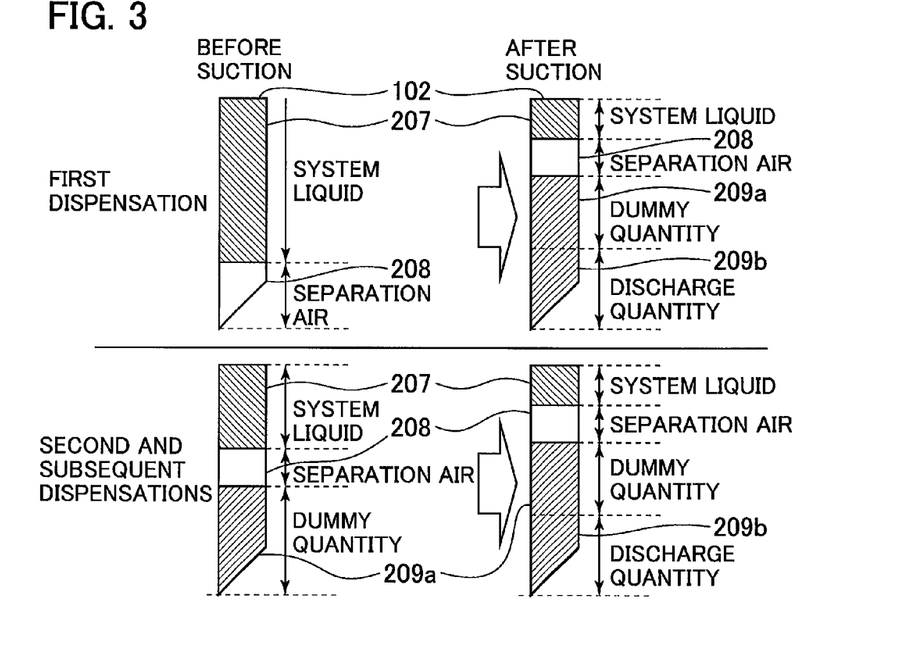
FIG. 3 is a schematic diagram showing changes in the state inside a sample probe from a time just before the start of the suction to a time just after the end of the suction.

FIG. 3 is a schematic diagram showing changes in the state inside the sample probe 102 from a time just before the start of the suction to a time just after the end of the suction.

When there are measurement requests for two or more analysis items (analytical assays) in regard to the same sample, the sample dispensation is carried out according to the number of analysis items. Referring to FIG. 3, in the first dispensation of the same sample, suction of a dummy quantity 209a in addition to a discharge quantity 209b is performed for the purpose of preventing the dilution of the sample. In the second and subsequent dispensations, the sucking and discharging operations are repeated while keeping the dummy quantity 209a inside the sample probe 102. The suction of the dummy quantity is generally performed for 6-12 μl. Since the dummy quantity 209a is sucked in additionally in the first dispensation, the detection of the dispensation abnormality based on the pressure fluctuation at the time of suction is easier in the first dispensation compared to the second and subsequent dispensations even though the quantity of dispensation (dispensation quantity) is the same. In contrast, in the second and subsequent dispensations in which the suction of the dummy quantity 209a is not performed, it is difficult to detect the dispensation abnormality based on the pressure fluctuation at the time of suction. In the present invention, the abnormality detection performance in the second and subsequent dispensations is improved by incorporating the pressure fluctuation information acquired in the first dispensation into the abnormality judgment in the second and subsequent dispensations.

Figure 4:
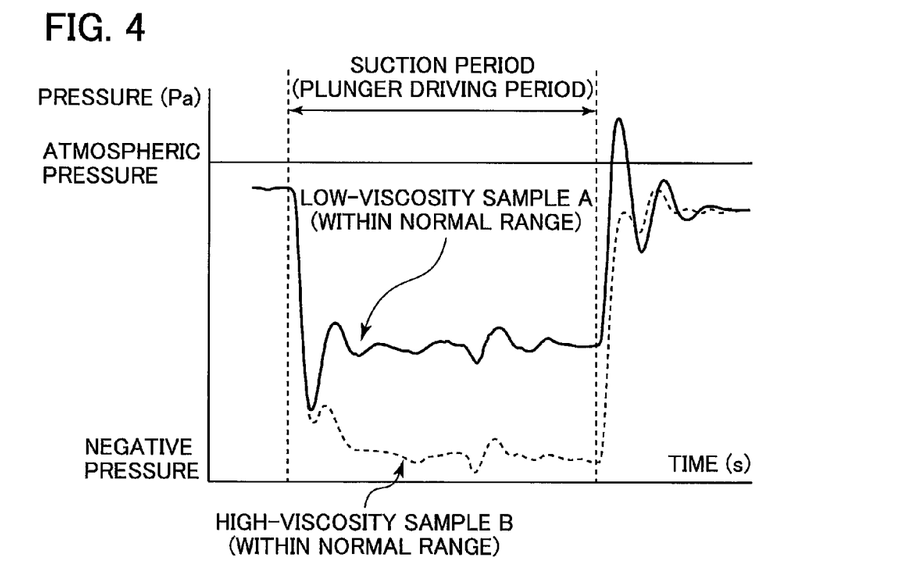
FIG. 4 shows the outline of the output of a pressure sensor at the time of sample suction.

FIG. 4 shows the outline of the output of the pressure sensor 118 at the time of sample suction.

In FIG. 4, the vertical axis represents the pressure as the output of the pressure sensor 118 and the horizontal axis represents the time. In the waveforms shown in FIG. 4, the solid line indicates the pressure fluctuation when a low-viscosity sample A (within a normal range) was sucked in, while the broke line indicates the pressure fluctuation when a high-viscosity sample B (within the normal range) was sucked in. It can be seen in FIG. 4 that the amount of change in the pressure and the appearance of vibration vary depending on the viscosity of the sample.

As shown in FIG. 4, in the high-viscosity sample B, the amount of change in the pressure (from the pressure value before the start of the suction to the pressure value during the suction) is greater and the vibration just after the start of the suction and the vibration just after the end of the suction are more suppressed in comparison with the low-viscosity sample A. As above, a variety of pressure fluctuation patterns can appear even in the suction of normal samples. Especially when the suction is performed in a condition with a small suction quantity, the amount of acquirable information decreases due to the short suction period. Accordingly, there are cases where it is difficult to discriminate between the suction of a bubble in the high-viscosity sample B (with the viscosity being within the normal range) and the suction of the low-viscosity sample A in a case where a minute foreign object is sucked in (with the viscosity being within the normal range). However, in order to carry out the abnormality detection with high accuracy, it is desirable to judge either or both of the above cases as abnormal. For this purpose, approximate viscosity of the sample is estimated in the first suction and the abnormality judgment in the second and subsequent sample dispensations is made by selecting optimum reference data (for the normality/abnormality judgment) based on the estimated viscosity. The details will be explained later.

The estimation of the viscosity is performed in the first suction for the following reason: In the first suction including the suction of the dummy quantity, the suction quantity is larger than the actual discharge quantity, and thus the suction period is longer than that in other cases not including the suction of the dummy quantity. The longer suction period is suitable for the estimation of differential pressure which will be explained later (i.e., the viscosity of the sample as the object of suction).

Figure 5:
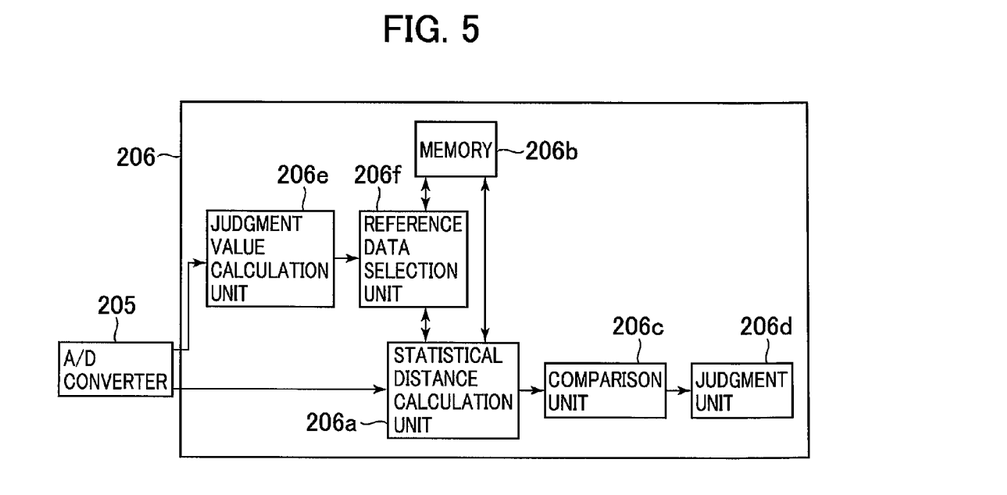
FIG. 5 is a block diagram showing the internal configuration of a signal processor in the first embodiment of the present invention.

FIG. 5 is a block diagram showing the internal configuration of the signal processor 206 in the first embodiment.

Referring to FIG. 5, the signal processor 206 includes a judgment value calculation unit 206e, a reference data selection unit 206f, a statistical distance calculation unit 206a, a memory 206b, a statistical distance calculation unit 206a, a comparison unit 206c, and a judgment unit 206d. The judgment unit 206d of the signal processor 206 transmits the result of the judgment to the controller 115. The signal processor 206 may either be provided separately from the controller 115 or inside the controller 115.

Figure 6:
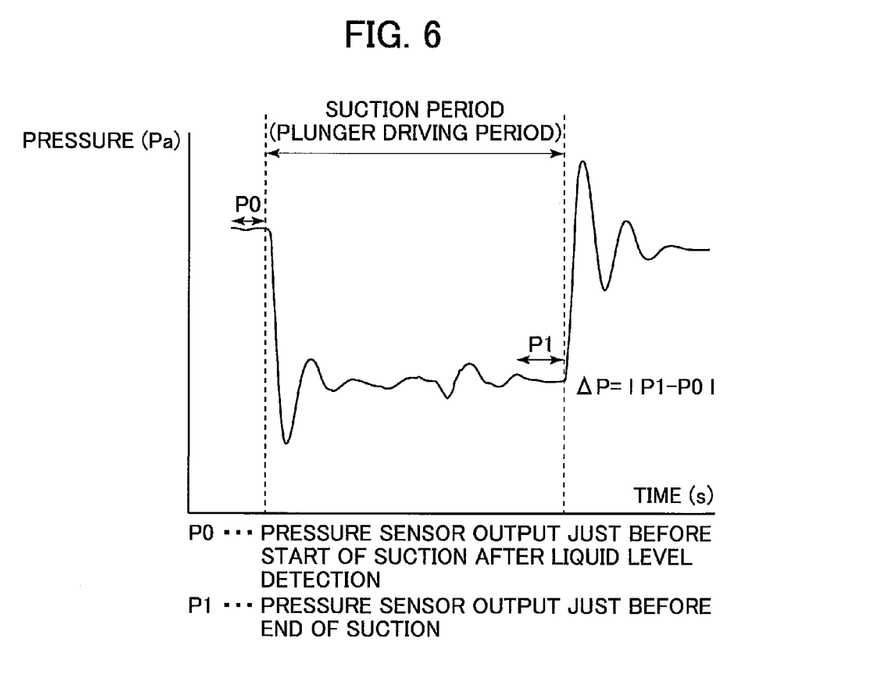
FIG. 6 is a schematic diagram showing an example of calculation of a judgment value by a judgment value calculation unit in the first embodiment of the present invention.

FIG. 6 is a schematic diagram showing an example of the calculation of a judgment value by the judgment value calculation unit 206e. In FIG. 6, "P0" represents the output of the pressure sensor 118 when the suction has not been performed yet (just after the detection of the sample liquid level). The output of the pressure sensor 118 in this state takes on values influenced by the atmospheric pressure.

In FIG. 6, "P1" represents the output of the pressure sensor 118 just before the end of the suction. The influence of the atmospheric pressure can be avoided by calculating the differential pressure ΔP between P0 and P1. In a dispensation quantity range in which the driving pattern of the drive mechanism 201 (motor) remains the same, the differential pressure ΔP between P0 and P1 reflects the viscosity of the sample. Since the output value of the pressure sensor 118 usually fluctuates finely, it is desirable to set each of P0 and P1 at the average value in a certain period.

Figure 7:
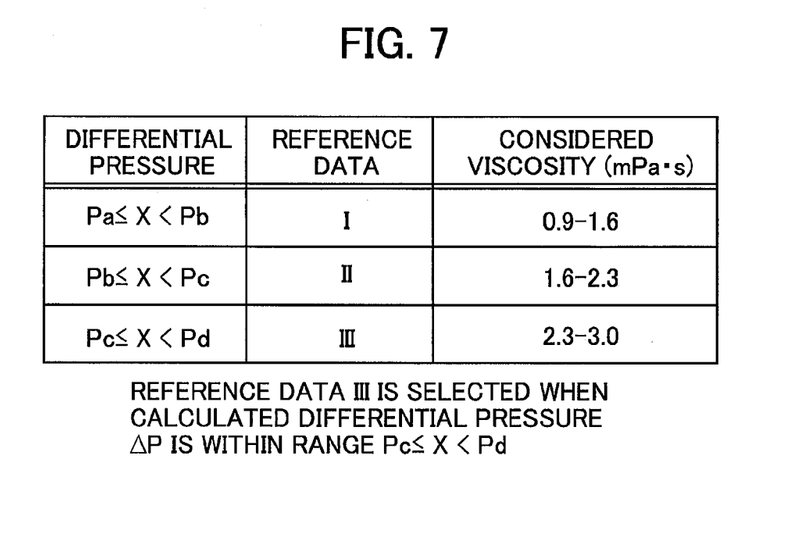
FIG. 7 is a table showing an example of selection of reference data by a reference data selection unit in the first embodiment of the present invention.

FIG. 7 is a table showing an example of the selection of the reference data by the reference data selection unit 206f. In the example of FIG. 7, the reference data selection unit 206f makes a selection from multiple pieces of stored reference data by using the judgment value calculated by the judgment value calculation unit 206e.

In this example, three pieces of reference data have been prepared, from which a piece of reference data is selected based on the judgment value. Each piece of reference data has been prepared for each dispensation quantity or each dispensation quantity range as a result of calculation of characteristic variables.

When the differential pressure is higher than or equal to Pa and lower than Pb, the reference data I is selected. In this case, the viscosity being considered is within a range of 0.9-1.6 mPa·s. When the differential pressure is higher than or equal to Pb and lower than Pc, the reference data II is selected. In this case, the viscosity being considered is within a range of 1.6-2.3 mPa·s. When the differential pressure is higher than or equal to Pc and lower than Pd, the reference data III is selected. In this case, the viscosity being considered is within a range of 2.3-3.0 mPa·s.

The statistical distance D calculated by the statistical distance calculation unit 206a is an index obtained by digitizing the similarity between two events (typified by a plurality of characteristic variables). In the first embodiment of the present invention, the calculation is made to determine how distant the data measured at that time is from the set of the reference data. There are a lot of methods for the calculation of the statistical distance D, such as the Mahalanobis distance, the Euclidean distance, the standardized Euclidean distance, the Manhattan distance, the Chebyshev distance, the Minkowski distance, and the multivariate normal density.

Figure 8:
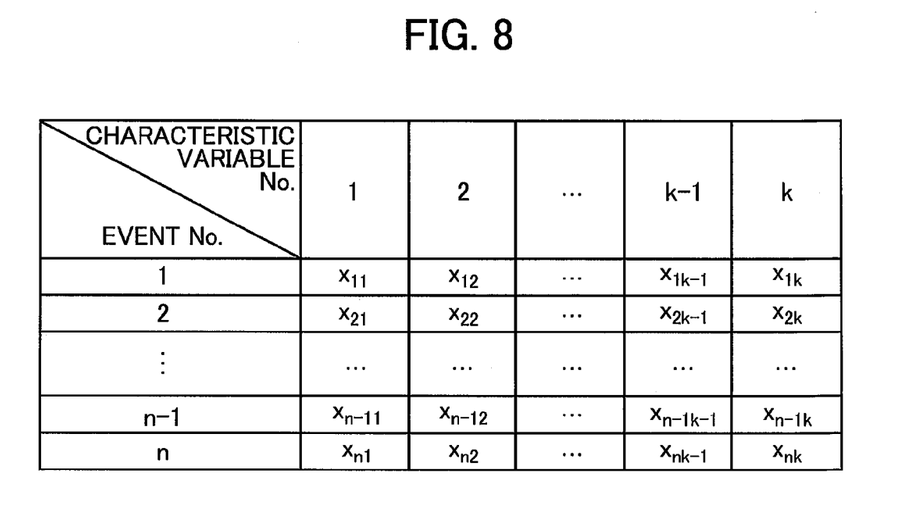
FIG. 8 is a table showing an example of reference data used for calculation of Mahalanobis distance in the first embodiment of the present invention.

For example, the Mahalanobis distance D is calculated as follows:

FIG. 8 is a table showing an example of the reference data used for the calculation of the Mahalanobis distance in the first embodiment of the present invention.

As shown in FIG. 8, assuming that there are characteristic variable numbers 1-k and event numbers 1-n, the reference data for the event number 1 are expressed as $x_{11}, \ldots, x_{1k}$. The reference data for the event number n are expressed as $x_{n1}, \ldots, x_{nk}$.

Each characteristic variable $x_1, x_2, \ldots, x_k$ as the object of the judgment is normalized by performing calculation according to the following expression (1) by use of the average $x'_1, x'_2, \ldots, x'_k$ (a bar is attached to each variable x in the expression (1)) and the standard deviation $\sigma_1, \sigma_2, \ldots, \sigma_k$ of each characteristic variable $x_1, x_2, \ldots x_k$ in the reference data:

$$X_i = \frac{x_i - \bar{x}_i}{\sigma_i} \quad (1)$$

In the above expression (1), "i" represents an integer (i=1, 2, . . . , k).

A correlation matrix representing the correlations between the characteristic variables is determined from the reference data. The Mahalanobis distance D is calculated according to the following expression (2) by use of the inverse matrix A of the correlation matrix and the normalized characteristic variables:

$$D = \sqrt{\frac{1}{k}(X_1 \cdots X_k)A \begin{pmatrix} X_1 \\ \vdots \\ X_k \end{pmatrix}} \quad (2)$$

Figure 9:
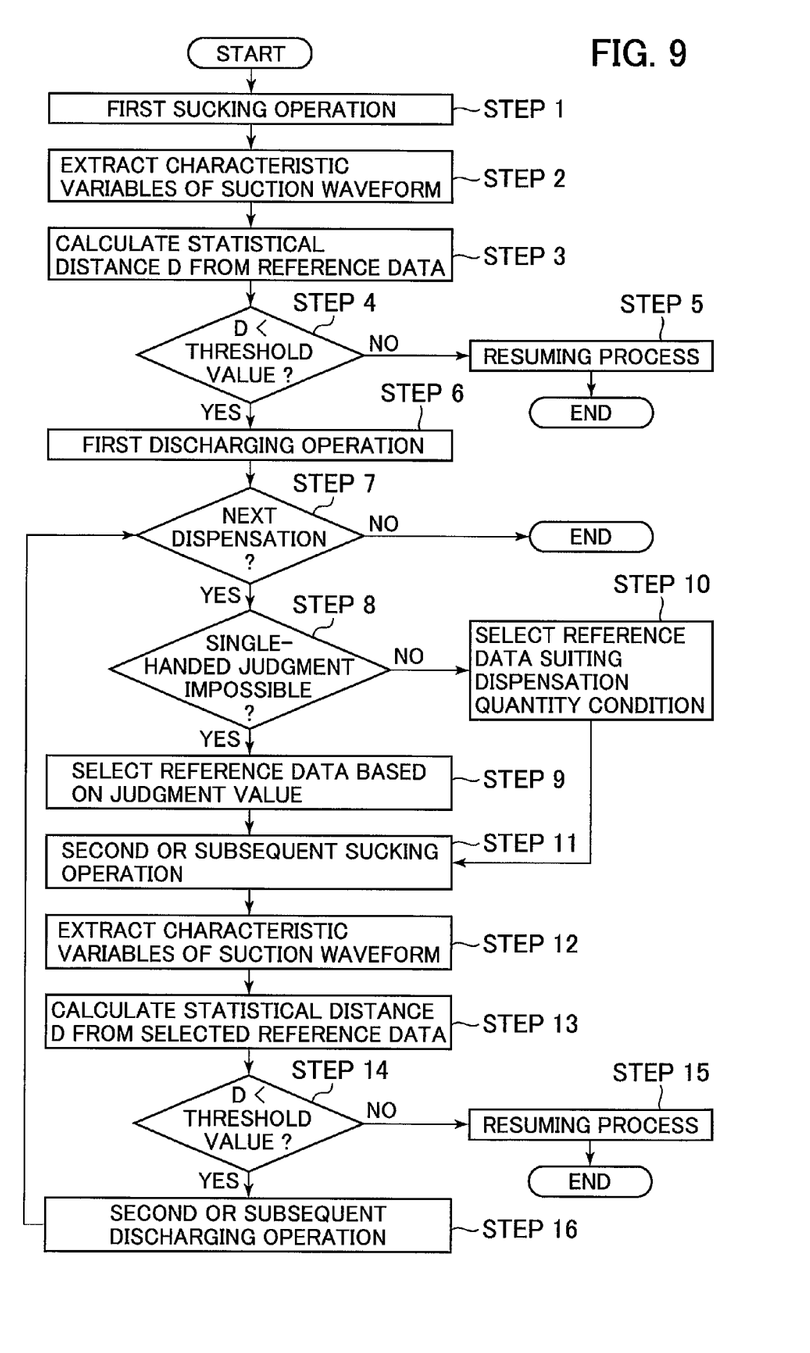
FIG. 9 is a flow chart of a discriminating operation in the first embodiment of the present invention.

FIG. 9 is a flow chart of a discriminating operation in the first embodiment of the present invention.

Referring to FIG. 9, the sample probe 102 performs the sucking operation in the first dispensation (STEP 1). Subsequently, the statistical distance calculation unit 206a calculates the characteristic variables in regard to the pressure waveform digital signal sent from the A/D converter 205 (STEP 2).

The characteristic variables calculated in this step can be variables of any type as long as the pattern of the pressure fluctuation can be expressed accurately. For example, average pressure values at certain time intervals, timing of appearance of local minimum points and local maximum points of the pressure fluctuation (appearing at the times of starting and stopping the movement of the plunger 202), etc. may be used as the characteristic variables.

The signal processor 206 has previously stored a result of calculation of characteristic variables (in a case where the sample probe 102 succeeded in normally dispensing the sample) in the memory 206b as the reference data. The statistical distance calculation unit 206a calculates the statistical distance D of the calculated characteristic variables from the reference data (STEP 3).

Then, the comparison unit 206c compares the statistical distance D with a preset threshold value (threshold value for the judgment on whether there was an abnormality in the suction of the sample by the sample probe) stored in the memory 206b (STEP 4). The result of the comparison is supplied to the judgment unit 206d.

If the statistical distance D is greater than the preset threshold value, the judgment unit 206d judges that there was an abnormality in the suction. In this case, a resuming process 1 is performed (STEP 5). In the resuming process 1, the judgment unit 206d informs the controller 115 and the computer 114 of the existence of the suction abnormality, and an alarm process (e.g., displaying an alarm on the display screen (abnormality notification unit) of the computer 114) and an operation for advancing to the processing of the next sample are performed under the control of the controller 115 and the computer 114.

If the statistical distance D is less than the threshold value in the STEP 4, the first discharging operation (STEP 6) is performed under the control of the controller 115 according to a command from the judgment unit 206d. Subsequently, a judgment is made on whether the next (second or subsequent) dispensation has been ordered or not (STEP 7). If the next (second or subsequent) dispensation has not been ordered, the process is ended. If the next (second or subsequent) dispensation has been ordered in the STEP 7, the controller 115 judges whether a single-handed judgment is possible of not based on a dispensation normality/abnormality judgment minimum quantity (explained later) (STEP 8). The dispensation normality/abnormality judgment minimum quantity has previously been stored in the memory 206b as a threshold value of the dispensation quantity. This judgment is made by judging whether the planned suction quantity is larger than or equal to the threshold value or smaller than the threshold value (or, larger than the threshold value or smaller than or equal to the threshold value). If the single-handed judgment is possible (i.e., if the planned suction quantity is larger than or equal to the threshold value) in the STEP 8, the controller 115 determines to command the signal processor (signal processing unit) 206 to select reference data suiting the dispensation quantity condition at that time (STEP 10). Thereafter, the process advances to STEP 11. The judgment in the STEP 8 is made for the following reason: When the dispensation quantity in the second or subsequent dispensation is large, the judgment on the presence/absence of the suction abnormality can be made by using preset reference data suiting the dispensation quantity condition, without the need of selecting a piece of reference data from multiple pieces of reference data at the same dispensation quantity (e.g., the reference data I, the reference data II, and the reference data III).

If the single-handed judgment is impossible (i.e., if the planned suction quantity is smaller than the threshold value) in the STEP 8, the reference data selection unit 206f is commanded by the controller 115 to select the reference data based on the dispensation quantity and the judgment value (differential pressure ΔP) used in the first sucking operation (STEP 9).

Subsequently, the second or subsequent sucking operation of the same sample is carried out (STEP 11). When the selection of reference data by the STEP 10 has been determined, reference data suiting the dispensation quantity condition is selected by the judgment value calculation unit 206e and the reference data selection unit 206f. Then, the statistical distance calculation unit 206a calculates (extracts) the characteristic variables in regard to the pressure waveform digital signal sent from the A/D converter 205 (STEP 12). Subsequently, the statistical distance calculation unit 206a calculates the statistical distance D of the calculated characteristic variables from the selected reference data (STEP 13). Then, the comparison unit 206c compares the statistical distance D with the preset threshold value stored in the memory 206b and supplies the result of the comparison to the judgment unit 206d. Specifically, whether the statistical distance D is less than the threshold value or not is judged (STEP 14).

If the statistical distance D is the preset threshold value or more, the judgment unit 206d judges that there was an abnormality in the suction. In this case, a resuming process 2 is performed (STEP 15). In the resuming process 2, the judgment unit 206d informs the controller 115 and the computer 114 of the existence of the suction abnormality, and the alarm process and an operation for advancing to the processing of the next sample (analyte) are performed under the control of the controller 115 and the computer 114.

If the statistical distance D is less than the threshold value in the STEP 14, the control by the controller 115 shifts to the discharging operation according to a command from the judgment unit 206d (STEP 16). Thereafter, the sequence from the STEP 7 to the STEP 16 is repeated till the end of the next dispensation.

Figures 10, 11:
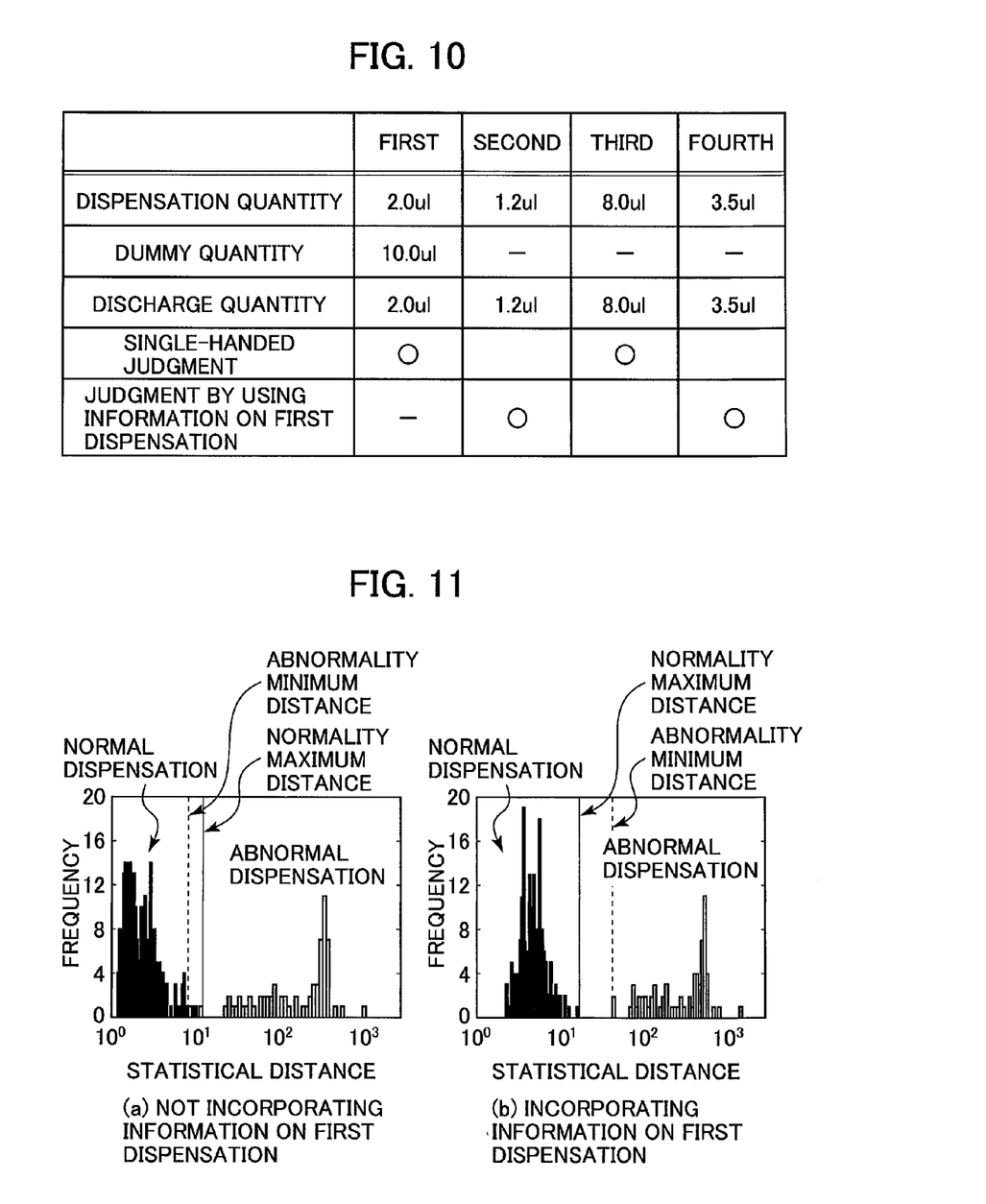
FIG. 10 is a table showing an example of data (dispensation quantity in each dispensation, etc.) in an actual analysis in the first embodiment of the present invention.
FIG. 11 is a graph comparing the accuracy of abnormality judgment between an example employing the present invention and an example not employing the present invention.

FIG. 10 is a table showing an example of application of the first embodiment of the present invention to the actual analysis. Shown in FIG. 10 is an example of data (dispensation quantity, dummy quantity, discharge quantity, whether the single-handed judgment is possible or not, whether or not to make the judgment by using information on the first dispensation) in regard to each dispensation. In the example of FIG. 10, a dispensation quantity with which the single-handed dispensation normality/abnormality judgment (STEP 8 in FIG. 9) is possible (dispensation normality/abnormality judgment minimum quantity) is previously determined experimentally and this dispensation quantity is used as a preset value.

In this example, the minimum quantity with which the single-handed dispensation normality/abnormality judgment is possible is assumed to have been set at 4.0 μl. The dummy quantity in this example is assumed to be 10.0 μl. In the first dispensation, the suction of the dummy quantity is performed in addition to the suction of a discharge quantity of 2.0 μl. When the result of the single-handed dispensation normality/abnormality judgment is normal, the differential pressure ΔP is stored in the memory 206b for the selection of the reference data used for the normality/abnormality judgment regarding the second and subsequent dispensations.

In the second dispensation, suction of a discharge quantity of 1.2 μl is performed. Since the discharge quantity is less than the single-handed dispensation normality/abnormality judgment minimum quantity 4.0 μl, the judgment is made by using the information on the first dispensation. This judgment is made by using the reference data selected based on the differential pressure ΔP in the first dispensation and the dispensation quantity in the second dispensation.

In the third dispensation, suction of a discharge quantity of 8.0 μl is performed. Since the discharge quantity is larger than the single-handed dispensation normality/abnormality judgment minimum quantity 4.0 μl, the judgment by using the information on the first dispensation is unnecessary. Thus, the normality/abnormality judgment in this case is made by means of the single-handed judgment. In the fourth dispensation, suction of a discharge quantity of 3.5 μl is performed. Since the discharge quantity is less than the dispensation normality/abnormality judgment minimum quantity 4.0 μl, the judgment is made by using the information on the first dispensation. This judgment is made by using the reference data selected based on the differential pressure ΔP in the first dispensation and the dispensation quantity in the fourth dispensation.

While the dispensation normality/abnormality judgment minimum quantity was set in the example of FIG. 10, it is not necessarily essential to set such a quantity; the selection of the reference data may be made uniformly based on the judgment value (STEP 9 in FIG. 9), that is, the STEP 8 in FIG. 9 may be omitted. However, setting the minimum quantity eliminates the need of previously storing multiple pieces of reference data (for dispensation quantities larger than the minimum quantity) in the in the memory 206b. Consequently, reduction in the capacity of the memory 206b becomes possible.

FIG. 11 is a graph comparing the accuracy of the abnormality judgment between an example employing the present invention and an example not employing the present invention. FIG. 11(a) shows the example not employing the present invention (not incorporating the information on the first dispensation), while FIG. 11(b) shows the example employing the present invention (incorporating the information on the first dispensation).

In the example of FIG. 11(a), there exists an overlapping part between a normality maximum distance and an abnormality minimum distance in the statistical distance, that is, there are cases where an abnormal dispensation is judged to be normal or a normal dispensation is judged to be abnormal.

In contrast, in the example of FIG. 11(b) employing the present invention, there exists no overlapping part between the normality maximum distance and the abnormality minimum distance in the statistical distance. It can be seen that abnormal dispensations and normal dispensations are clearly discriminated from each other.

As described above, according to the first embodiment of the present invention, it is possible to implement an automatic analyzer capable of performing highly reliable analysis by accurately detecting the dispensation abnormality even in dispensation conditions with small suction quantities in the second and subsequent dispensations.

Incidentally, while the application of the present invention to the pressure fluctuation at the time of suction has been described in the above first embodiment, the present invention is also similarly applicable to the pressure fluctuation at the time of discharge.

Second Embodiment

Next, a second embodiment of the present invention will be described below. In the following description of the second embodiment, illustration and detailed explanation of configurations and operations in common with those in the first embodiment are omitted for brevity. Specifically, the configurations and operations shown in FIGS. 1-3 explained in the first embodiment are employed also in the second embodiment in a similar manner.

The second embodiment differs from the first embodiment as follows: In the first embodiment, the normality/abnormality judgment regarding the second or subsequent dispensation is made by selecting the reference data suitable for the normality/abnormality judgment regarding the second or subsequent dispensation based on the information obtained from the pressure fluctuation at the time of the first sucking operation and determining the statistical distance between the reference data and the object of the judgment. In the second embodiment, the dispensation normality/abnormality judgment is made based on information as a combination of the characteristic variables of the pressure fluctuation at the time of the first sucking operation (the sucking operation in the first dispensation) and the characteristic variables of the pressure fluctuation at the time of each subsequent sucking operation (the sucking operation in each subsequent dispensation).

Figure 12:
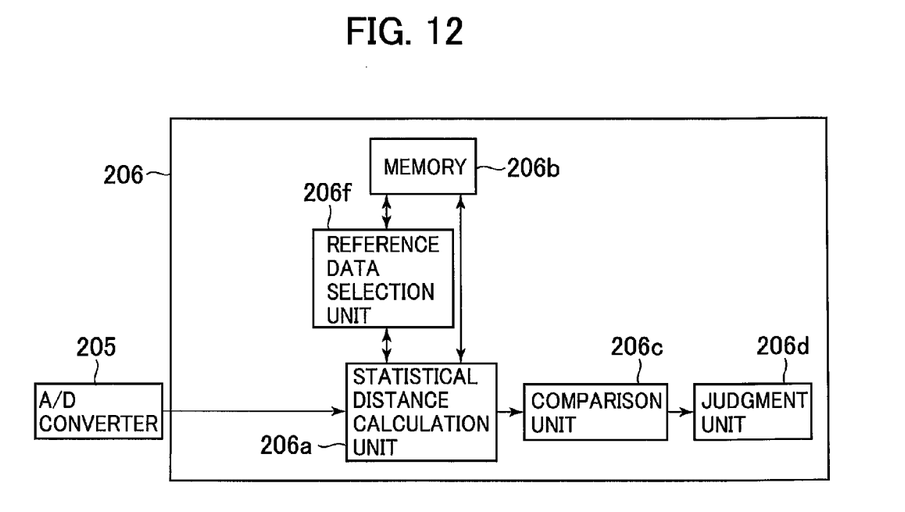
FIG. 12 is a block diagram showing the internal configuration of a signal processor in a second embodiment of the present invention.

FIG. 12 is a block diagram showing the internal configuration of a signal processor 206 in the second embodiment of the present invention. Referring to FIG. 12, the signal processor 206 includes a statistical distance calculation unit 206a, a memory 206b, a comparison unit 206c, a judgment unit 206d, and a reference data selection unit 206f.

The judgment unit 206d of the signal processor 206 transmits the result of the judgment to the controller 115. The signal processor 206 may either be provided separately from the controller 115 or inside the controller 115. When the sucking operation in the first dispensation is performed, the statistical distance calculation unit 206a calculates the characteristic variables in regard to the pressure waveform digital signal sent from the A/D converter 205. The characteristic variables calculated in this step can be variables of any type as long as the pattern of the pressure fluctuation can be expressed accurately. For example, average pressure values at certain time intervals, timing of appearance of local minimum points and local maximum points of the pressure fluctuation (appearing at the times of starting and stopping the operation of the plunger 202), etc. may be used as the characteristic variables.

Then, the statistical distance between the reference data stored in the memory 206b and the calculated characteristic variables is calculated. In the first sucking operation, the reference data selection unit 206f commands the statistical distance calculation unit 206a to select one from the multiple pieces of reference data stored in the memory 206b based on the suction quantity.

When the sample probe 102 succeeded in normally dispensing the sample, the result of the calculation of the characteristic variables at that time is stored as data in the memory 206b. Also in the second suction, the result of the calculation of the characteristic variables is stored as data in the memory 206b. The object of the judgment on whether the second sucking operation is normal or not is the data as the combination of the result of the calculation of the characteristic variables in the first dispensation and the result of the calculation of the characteristic variables in the second dispensation. Data as a combination of the reference data determined based on the dispensation quantity in the first dispensation and the reference data determined based on the dispensation quantity in the second dispensation is used as the reference data, and the judgment on whether the suction was normal or not is made by calculating the statistical distance of the aforementioned combined data of the characteristic variables from the reference data.

In the n-th sample suction (n: natural number greater than 1), the normality/abnormality judgment is made by using the data as the combination of the characteristic variables at the time of the first suction stored in the memory 206b and the characteristic variables at the time of the n-th suction as the object of the judgment, and by using the data as the combination of the reference data determined based on the dispensation quantity in the first dispensation and the reference data determined based on the dispensation quantity in the n-th dispensation as the reference data.

Figure 13:
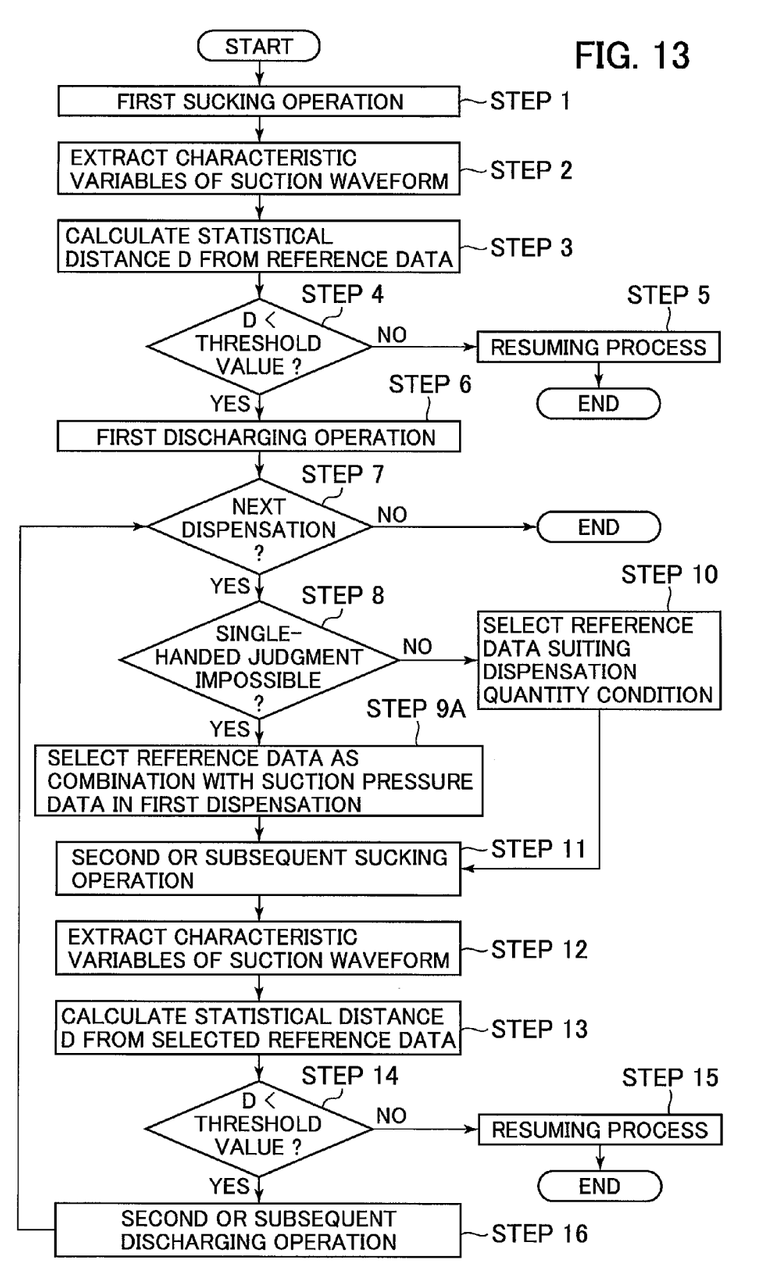
FIG. 13 is a flow chart of a discriminating operation in the second embodiment of the present invention.

FIG. 13 is a flow chart of a discriminating operation in the second embodiment of the present invention. The discriminating operation flow chart in the second embodiment differs from that in the first embodiment in that STEP 9A is executed instead of the STEP 9 in the first embodiment.

In the STEP 9A in FIG. 13, the data as the combination of the characteristic variables at the time of the normal first suction and the characteristic variables at the time of the n-th suction is used as the object of the judgment, and the reference data as the combination of the reference data determined based on the dispensation quantity in the first dispensation and the reference data determined based on the dispensation quantity in the n-th dispensation is selected. The other steps in the second embodiment are equivalent to those in the first embodiment. In the case where the single-handed judgment is possible in the STEP 8 (i.e., in the STEP 10), the use of the above-described combined data as the reference data and the judgment object data is unnecessary, and thus the STEP 10 is executed in the same way as in the first embodiment. Therefore, the handling of the reference data regarding the first dispensation and the characteristic variables regarding the first dispensation in the STEP 12 and the STEP 13 varies depending on the judgment in the STEP 8.

Figure 14:
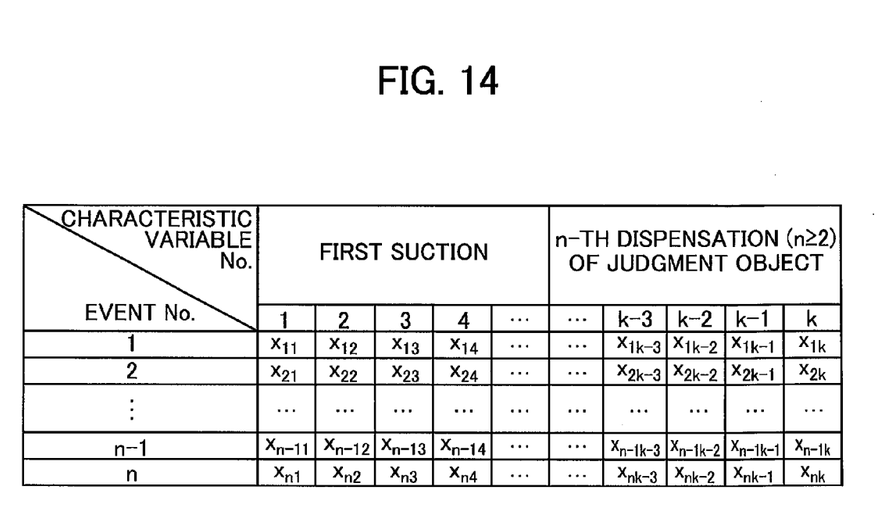
FIG. 14 is a table showing an example of reference data in the n-th dispensation in the second embodiment of the present invention.

FIG. 14 is a table showing an example of the combined reference data in the n-th dispensation in the second embodiment of the present invention. It can be seen that the amount of information has increased from the reference data in the n-th dispensation alone due to the addition of the reference data in the first dispensation. Accordingly, in the dispensation conditions with small suction quantities in the second and subsequent dispensations, the decrease in the amount of information due to the decrease in the suction quantity can be compensated for by use of the reference data in the first dispensation. Consequently, it is possible to implement an automatic analyzer capable of performing highly reliable analysis by accurately detecting the dispensation abnormality even in the dispensation conditions with small suction quantities in the second and subsequent dispensations.

As described above, effects similar to those of the first embodiment can be achieved in the second embodiment of the present invention.

Third Embodiment

Next, a third embodiment of the present invention will be described below. The third embodiment is a combination of the first and second embodiments. Similarly to the first embodiment, the reference data suitable for the normality/abnormality judgment in the n-th dispensation (n≥2) is selected from the multiple pieces of prestored reference data based on the information on the pressure fluctuation at the time of the first sucking operation. Further, similarly to the second embodiment, the reference data selected in this step is the data as the combination of the reference data in the first sucking operation and the previously selected reference data. On the other hand, the object of the judgment is the combination of the characteristic variables of the suction pressure data in the first dispensation and the characteristic variables of the suction pressure data in the n-th dispensation similarly to the second embodiment.

In the normality/abnormality judgment in the n-th dispensation (n≥2), if the single-handed judgment is possible, the reference data matching the dispensation quantity condition is selected. If the single-handed judgment is impossible, a piece of pattern data is formed by combining the characteristic variables calculated from the pressure fluctuation at the time of the first suction and the characteristic variables calculated from the pressure fluctuation at the time of the n-th suction. Then, the statistical distance between this pattern data and the selected reference data is calculated. The normality/abnormality of the dispensation is judged by the comparison between the calculated statistical distance and the threshold value.

The internal configuration of the signal processor 206 and the other configurations in the third embodiment are equivalent to those in the second embodiment.

Also in the third embodiment of the present invention, effects similar to those of the first and embodiments can be achieved.

Incidentally, the present invention is applicable not only to biochemical automatic analyzers but also to immunological automatic analyzers.

Further, the present invention is equally applicable not only to the pressure fluctuation at the time of suction but also to the pressure fluctuation at the time of discharge.

DESCRIPTION OF REFERENCE CHARACTERS

100 sample vessel
101 sample disk
102 sample probe
103 reagent vessel
104 first reagent disk
105 first reagent probe
106 second reagent disk
107 second reagent probe
108 stirring device
109 vessel cleaning mechanism
110 reaction vessel
111 reaction disk
112 light source
113 spectroscopic detector
114 computer
115 controller
116 dispensation channel
117 metering pump
118 pressure sensor
200 restrictor part
201 drive mechanism
202 plunger
203 valve
204 pump
205 A/D converter
206 signal processor
206*a* statistical distance calculation unit
206*b* memory
206*c* comparison unit
206*d* judgment unit
206*e* judgment value calculation unit
206*f* reference data selection unit
207 system liquid
208 separation air
209 sucked liquid

The invention claimed is:

1. An automatic analyzer comprising:
a sample probe which sucks in a sample stored in a sample vessel and discharges the sample into one or more reaction vessels;
a reagent probe which sucks in a reagent stored in a reagent vessel and discharges the reagent into the one or more reaction vessels;
an analysis unit which analyzes the sample in the one or more reaction vessels;
a pressure sensor which detects a pressure in the sample probe;
a signal processing unit which is configured to:
acquire suction pressure data from the pressure sensor during a suction period in a first dispensation where the sample is sucked in from the sample vessel by the sample probe,
select a piece of normality/abnormality judgment reference data from multiple pieces of normality/abnormality judgment reference data based on a pressure difference in the suction pressure data in the first dispensation, wherein the pressure difference is a differential pressure between a first pressure detected by the pressure sensor in a period from a stoppage of the sample probe after detecting a liquid level of the sample and prior to the start of the suction period and a second pressure detected by the pressure sensor prior to the end of the suction period,
calculate characteristic variables of suction pressure data of the same sample detected by the pressure sensor during a suction period in an n-th dispensation where the same sample is sucked in from the sample vessel and discharged by the sample probe, where n is a natural number and n≥2,
judge whether or not there was an abnormality in the suction of the same sample by the sample probe in the n-th dispensation by comparing a statistical distance between the calculated characteristic variables and the selected piece of normality/abnormality judgment reference data to a predetermined threshold value,
when the abnormality is judged for the n-th dispensation, display an alarm, and
when the abnormality is not judged for the n-th dispensation, discharge the same sample into one of the reaction vessels for the n-th dispensation; and
a controller which controls the operation of the sample probe, the reagent probe, the analysis unit and the signal processing unit,
wherein the abnormality is judged for the n-th dispensation when the statistical distance is greater than the predetermined threshold value.

2. The automatic analyzer according to claim 1, wherein the signal processing unit is further configured to:
when a suction quantity of the sample to be sucked in during the suction period in the n-th dispensation is less than a prescribed quantity, select the piece of normality/abnormality judgment reference data based on the pressure difference and the suction quantity of the sample in the n-th dispensation,
when the suction quantity of the sample sucked in the during the suction period in the n-th dispensation is equal to or greater than the prescribed quantity, select the piece of normality/abnormality judgment reference data based only on the suction quantity of the sample to be sucked in the n-th dispensation.

3. The automatic analyzer according to claim 2, wherein the signal processing unit includes:
- a memory which stores the multiple pieces of the normality/abnormality judgment reference data which are preset for each of a plurality of sample suction quantities, the suction pressure data of the first dispensation, and the predetermined threshold value.

4. The automatic analyzer according to claim 3, wherein the multiple pieces of the normality/abnormality judgment reference data stored in the memory are pressure waveform data for a plurality of normal suction periods of the sample that correspond to a plurality of different viscosities of the sample.

5. The automatic analyzer according to claim 3, wherein the statistical distance is selected from a Mahalanobis distance, a Euclidean distance, a standardized Euclidean distance, a Manhattan distance, a Chebyshev distance, a Minkowski distance, and a multivariate normal density.

* * * * *